(12) United States Patent
Ross et al.

(10) Patent No.: US 9,271,757 B2
(45) Date of Patent: Mar. 1, 2016

(54) AUTOMATED GROWING ROD DEVICE

(71) Applicant: AMB Surgical, LLC, Fishers, IN (US)

(72) Inventors: Tyson Ross, Franklin, OH (US); Casel Burnett, Walton, OH (US)

( * ) Notice: Subject to any disclaimer, the term of this patent is extended or adjusted under 35 U.S.C. 154(b) by 0 days.

(21) Appl. No.: 14/076,183

(22) Filed: Nov. 9, 2013

(65) Prior Publication Data

US 2015/0250505 A1  Sep. 10, 2015

Related U.S. Application Data

(63) Continuation of application No. 13/072,684, filed on Mar. 26, 2011, now Pat. No. 8,585,740, which is a continuation-in-part of application No. 13/004,752, filed on Jan. 11, 2011, now abandoned.

(60) Provisional application No. 61/294,444, filed on Jan. 12, 2010.

(51) Int. Cl.
    *A61B 17/70* (2006.01)
    *A61B 17/66* (2006.01)

(52) U.S. Cl.
    CPC ............ *A61B 17/7016* (2013.01); *A61B 17/66* (2013.01); *A61B 17/7004* (2013.01); *A61B 17/7044* (2013.01)

(58) Field of Classification Search
    CPC ........... A61B 17/7016; A61B 17/7014; A61B 17/7019; A61B 17/7025; A61B 17/7052; A61B 17/7216; A61B 17/8004; A61B 17/8023
    See application file for complete search history.

(56) References Cited

U.S. PATENT DOCUMENTS

| | | | | |
|---|---|---|---|---|
| 5,330,477 A | * | 7/1994 | Crook | 606/33 |
| 5,704,939 A | * | 1/1998 | Justin | 606/63 |
| 8,016,859 B2 | * | 9/2011 | Donofrio et al. | 606/246 |
| 2004/0023623 A1 | * | 2/2004 | Stauch et al. | 455/115.1 |
| 2007/0250098 A1 | * | 10/2007 | Malackowski et al. | 606/170 |
| 2007/0265645 A1 | * | 11/2007 | Birk et al. | 606/157 |
| 2010/0249928 A1 | * | 9/2010 | Schwab | 623/13.14 |

* cited by examiner

*Primary Examiner* — Eduardo C Robert
*Assistant Examiner* — Julianna N Harvey

(57) ABSTRACT

A remotely controllable growing rod device comprises a housing containing on-board electronics and at least one drive assembly operable to move associated extension elements relative to each other. Each extension element terminates in an anchor element configured to be anchored to a part of the spine, such as the pedicle of a vertebral body. The on-board electronics includes a microprocessor, a power supply, such as an inductive power supply, and a receiver/transmitter. The microprocessor is configured to receive remotely transmitted movement data through the receiver and is further configured for feedback controlled actuation of the drive assembly for relative movement the associated extension elements to achieve a desired physiological condition of the patient's spine.

13 Claims, 13 Drawing Sheets

AUTOMATED GROWING ROD DEVICE

PRIORITY CLAIM

This application is a continuation of and claims priority to utility patent application Ser. No. 13/072,684, filed on Mar. 26, 2011, which issued on Nov. 19, 2013, as U.S. Pat. No. 8,585,740, and which is a continuation-in-part and claims priority to utility patent application Ser. No. 13/004,752, filed on Jan. 11, 2011, now abandoned, the entire disclosure of which is incorporated herein by reference, which application claims priority to provisional application No. 61/294,444, filed on Jan. 12, 2010, now expired, the entire disclosure of which is incorporated herein by reference.

BACKGROUND

The present invention relates to a "growing rod" device, namely a device that is adapted to be mounted to a long bone or to the spine of a patient and that incorporates the ability to have its overall length extended (distracted) or reduced (compressed) in situ.

Growing rod devices have been developed for implantation in the spine of a child to correct an abnormal curvature of the spine, such as scoliosis. In devices of this type, a rod assembly is progressively lengthened to reduce the abnormal curvature while allowing the child's body to adapt to the revised spinal position. One typical growing rod device includes of a pair of axially aligned rods, each terminating in an anchor element configured for attachment to the spine. Lengthening of one or both rods requires a surgical procedure to advance the effective rod lengths, usually about every six months. This approach requires multiple surgeries, often over a multi-year period, with the result being the correction of the spine curvature caused by the onset of scoliosis.

While growing rod devices have demonstrated their value in correcting serious spinal deformities, the need for multiple surgeries is highly problematic. There is a significant need for a growing rod device that does not require surgical intervention to adjust the length of the device.

SUMMARY

In accordance with one feature, the present invention provides a growing rod device that may be remotely controlled while implanted within the patient, thereby eliminating the need for separate surgical procedures to adjust the length of the device. In one embodiment, the device comprises a housing containing on-board electronics and supporting drive assemblies operable to extend or retract associated extension elements projecting along the axis of the device. Each extension element terminates in an anchor element configured to be anchored to a part of the anatomy, such as the pedicle of a vertebral body or to a long bone. Each drive assembly includes a micromotor and a threaded interface between the motor and the corresponding extension element. In one embodiment a drive rotor is rotatably disposed within a stator that is fixed to the housing. The threaded interface between the drive rotor and the extension element converts rotation of the rotor to translation of the extension element for extension/distraction or compression of the spine or bony anatomy.

In a further aspect, the on-board electronics includes a microprocessor, a power supply and a receiver/transmitter. In one aspect the power supply is an inductive power supply that relies upon inductive energy transmission from an external device. The power supply may include a rechargeable battery that is inductively charged or may constitute a power converter that provides electrical power to the on-board electronics only when energized by the external inductive power source.

In another aspect, the on-board electronics of multiple growing rod devices implanted within a patient may communicate via a common data bus. The microprocessor of each such device has a unique address or identifier so that only control signals pertinent to the particular device are transmitted to or acknowledged by that device. The on-board electronics may also incorporate various condition sensors, such as rotation and translation sensors operable to determine movement of the drive assembly components, strain gages operable to transmit load data, and temperature sensors, for example.

A handheld programming unit is provided in another aspect of the invention. The handheld unit provides an external interface to the implanted growing rod device(s), in particular to communicate movement data to the devices and to receive data transmitted by the devices. The handheld unit interfaces with software, resident on the unit or in a separate computer, which permits generation of movement data for each growing rod device in a patient. On the handheld unit movement data may be directly input via a keypad. Alternatively or in addition, software may be provided that calculates movement data or a movement protocol. The software may incorporate GUI interface for interaction with the caregiver or caregiver/surgeon to generate the movement data or protocol. This movement information may be uploaded to the handheld unit or in some cases communicated directly to the implanted device.

DETAILED DESCRIPTION

Figure 1:
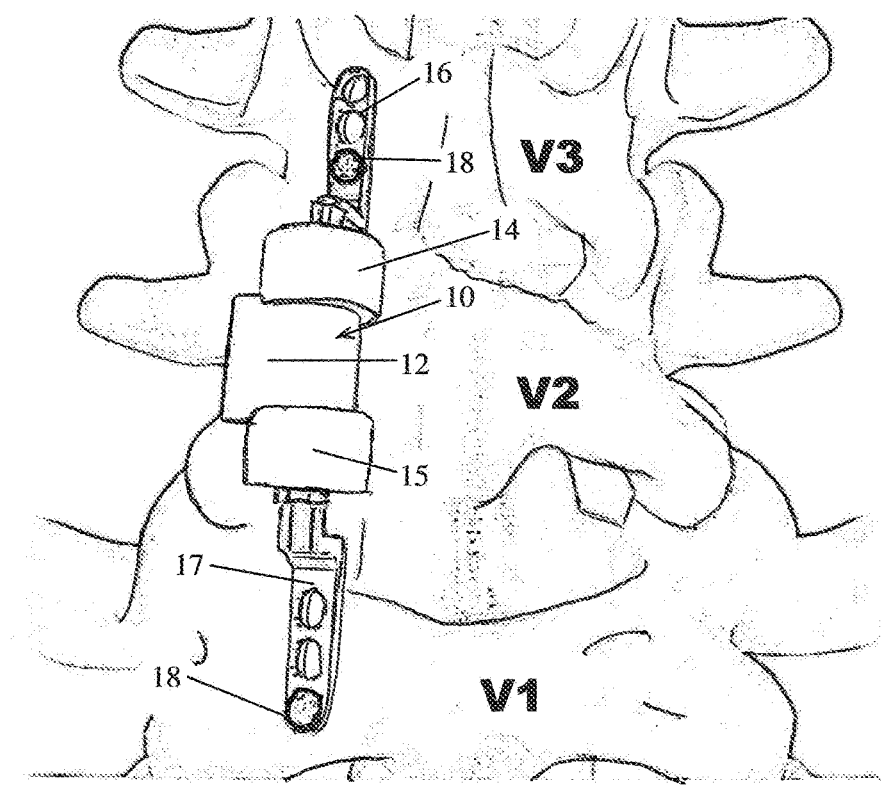
FIG. 1 is a depiction of a growing rod device according to the present invention mounted to the spine of a patient.
Figure 2:
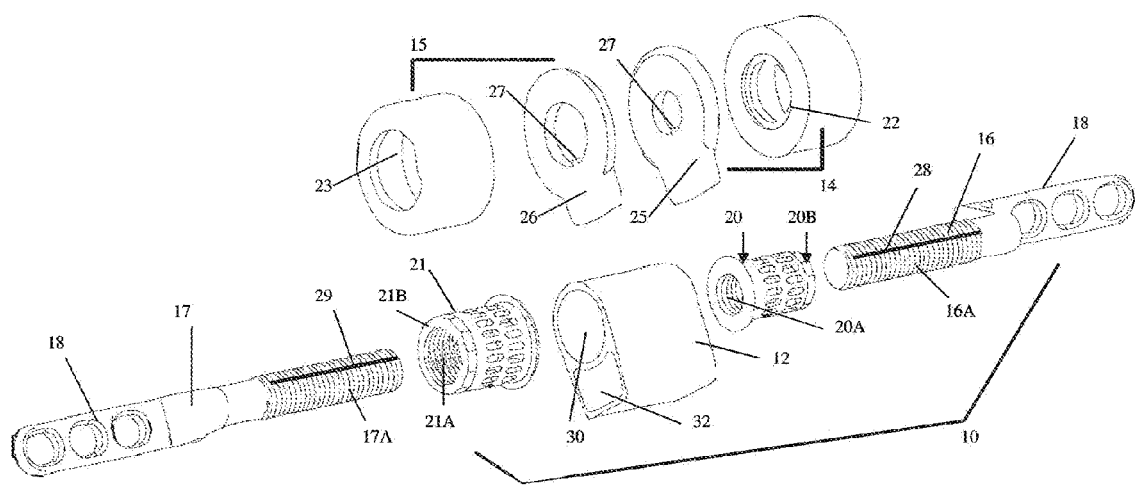
FIG. 2 is an exploded view of a growing rod device according to one embodiment of the invention.
Figure 3:
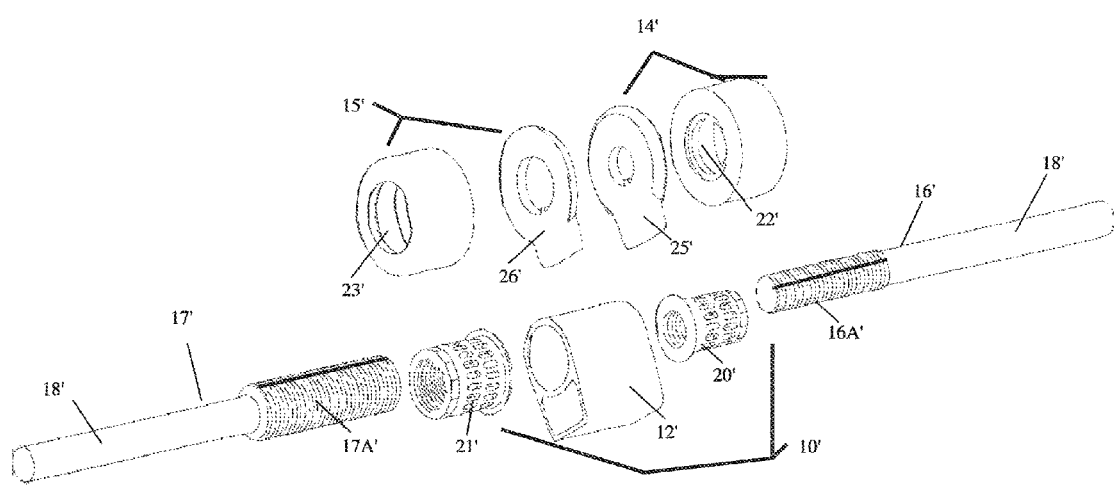
FIG. 3 is an exploded view of a growing rod device according to a further embodiment of the invention.

According to one embodiment, an automated growing rod device 10 includes a main housing 12 and two drive assemblies 14, 15 attached to opposite ends of the main housing, as shown in FIGS. 1-2. Extension elements 16, 17 project from opposite ends of the device, and may be coaxially aligned. The end of each extension element terminates in an anchor element 18, which may be a slotted plate, as shown in FIGS. 1-2, or an elongated rod, as shown in FIG. 3. In the embodiment shown in FIG. 1, the anchor elements 18 are fastened to a vertebral body V1, V3 by appropriate bone engaging fasteners, such as bone screws or bone bolts, with the device spanning the intermediate vertebra V2. It is understood that other bone engaging fasteners may be employed to engage an elongated rod anchor element to the spine.

As shown in FIG. 1, the growing rod assembly spans several vertebral levels, three in the illustrated embodiment. As explained herein, the growing rod device operates to drive the extension elements 16, 17 apart, lengthening the device 10 and thereby changing the angle of spine (i.e., the Cobb angle) at the instrumented levels, with the ultimate goal being to straighten the spine as much as possible.

In one embodiment, a growing rod device 10 includes extension elements 16, 17 in the form of elongated rods terminating at one end in the anchor element 18 and having a threaded shank 16a, 17a at the opposite end. The threaded shanks of the two extension elements are contained within the cavity 30 defined in the main housing 12. Each threaded shank is configured to engage an internally threaded bore 20a, 21a of a corresponding drive rotor 20, 21, as best seen in FIG. 2. The drive rotors 20, 21 form part of the drive assemblies 14, 15. The drive assemblies further include stator elements 22, 23 that operate to rotate the drive rotors when the drive assemblies 14, 15 are energized. The drive assemblies are mounted or fastened to the main housing 12 so that the stator elements remain fixed and non-rotating within the growing rod assembly 10. It can be appreciated that the stator elements and corresponding drive rotors are constructed as a conventional electromagnetic motor so that activation of the stator elements results in rotation of the drive rotors. As the drive rotor 20 rotates, the interface between the threaded bore 20a and the threaded shank 16a leads to translation of the extension element 16. Rotation of the drive rotor in one direction causes the extension element to extend away from the main housing 12, while an opposite rotation causes the extension element to retract within the housing. It can be appreciated that the stator 23, drive rotor 21 and threaded shank 17a work in the same way to extend or retract the opposite extension element 17.

The thread pitch of the threaded shanks 16a, 17a and rotor threaded bores 20a, 21a is preferably sized to permit finely tuned lengthening of the device. In addition, the thread pitch can help provide a mechanical advantage to provide the distraction force necessary to push instrumented vertebrae against the normal spinal loads. In certain procedures, the distraction force necessary for effective correction of a spinal deformity is at least 20 lbf. Distraction forces up to 45 lbf may be suitable for certain procedures. In a specific embodiment, the drive assemblies are capable of generating a torque of 40-50 in-ozs to achieve the required distraction force. In a specific embodiment, the threads of the extension elements and drive rotors may have a pitch of 40-50 tpi and a thread angle of about 2.5°. The thread angle may be preferably selected to minimize the torque generated by the drive assemblies, particularly since that torque must be reacted by the patient's anatomy. The extension elements may be formed of stainless steel, titanium, cobalt-chrome or other suitable medical grade material capable of withstanding the significant spinal loads without measurable bending or twisting. The extension elements may have a diameter of 0.5 in, or other diameters consistent with spinal implants. If the growing rod device 10 is used in other settings, such as for long bone lengthening, the extension elements may be appropriately sized.

In order to ensure that the extension elements only translate and do not rotate, an anti-rotation feature is incorporated into the drive assemblies and threaded shanks. In one embodiment, the drive assemblies 14, 15 include a corresponding anti-rotation washer 25, 26 interposed between the drive assemblies and the main housing 12. The washers include an inwardly projecting tang 27 that is configured to slidably fit within a groove 28, 29 in the threaded shanks 16a, 17a. Since the washers 25, 26 are fixed to the housing, the tangs 27 cannot rotate, and since the tangs are received within the grooves 28, 29 the extension elements 16, 17 cannot rotate. The tangs and grooves are sized to permit free relative sliding movement between the components, but are sufficiently tightly toleranced so that the amount of extension/retraction (or the overall length) of the growing rod assembly 10 can be precisely known. In other words, too much slop between the tang and groove can permit a small amount of angular movement of the extension element which translates to a slight change in axial position of the extension element.

Figure 4:
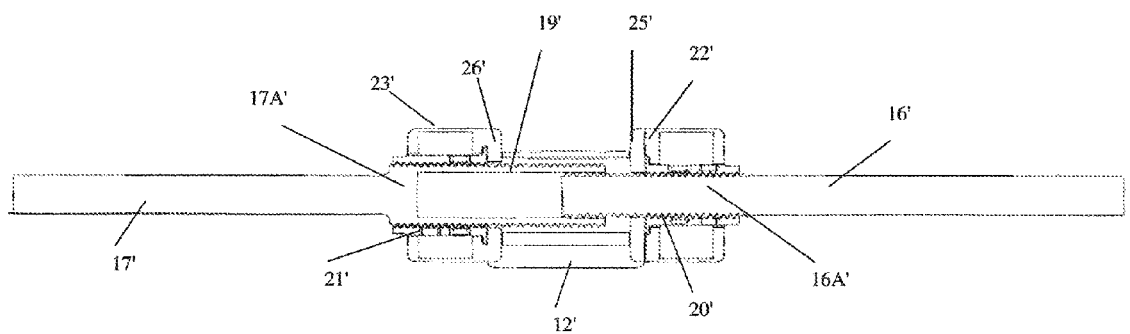
FIG. 4 is a side cross-sectional view of the growing rod device shown in FIG. 3.

Another embodiment is shown in FIGS. 3-4 in which a growing rod assembly 10' includes telescoping extension elements. The assembly 10' includes an extension element 17' having an elongated rod for the anchor element 18' and a hollow threaded shank 17a' at the opposite end. The hollow threaded shank 17a' defines an elongated cavity 19' that is sized to receive the threaded shank 16a' of the opposite extension element 16', as best shown in FIG. 4. This telescoping or overlapping feature allows the growing rod assembly 10' to have the same stroke or throw as the assembly 10 shown in FIG. 2, but in a smaller envelop. In the embodiment of FIG. 2, the two extension elements 14, 15 abut inside the main housing 12 when the extension elements are in their fully retracted position. On the other hand, when the extension elements 16', 17' of FIG. 4 are fully retracted the threaded shank 16a' of extension element 16' is positioned entirely within the cavity 19' of the other extension element. This feature allows the growing rod assembly 10' to have a fully retracted overall length that is less than the overall length of the assembly 10 by the length of the cavity 19'. This retracted length difference may permit the use of a smaller main housing 12' in the embodiment of FIGS. 3-4 over the other embodiment. More importantly, this overlap or telescoping feature allows the device to have a significantly smaller length when the device is being initially implanted within the patient. The smaller envelop simplifies the surgery and reduces the overall trauma to the patient when the device is implanted.

As illustrated in FIG. 3, the drive rotor 21' for the extension element 17' has a larger diameter than the drive rotor 20'. The drive rotors 20' and 21' are sized to receive the threaded shanks 16a' and 17a' threaded into the threaded bores 20a', 21a'. Thus, since the shank 16a' extends into the shank 17a' this latter shank is necessarily of a larger diameter, which thus requires a larger diameter drive rotor. The drive assembly 15 may be appropriately sized to accommodate the larger drive rotor 21'. Thus, the drive assembly 15' and stator 23' may be larger in profile than the opposite drive assembly 14' and stator 22'. Likewise, the anti-rotation washers 25' and 26' are sized to receive the corresponding threaded shank 16a', 17a'.

Figure 5:
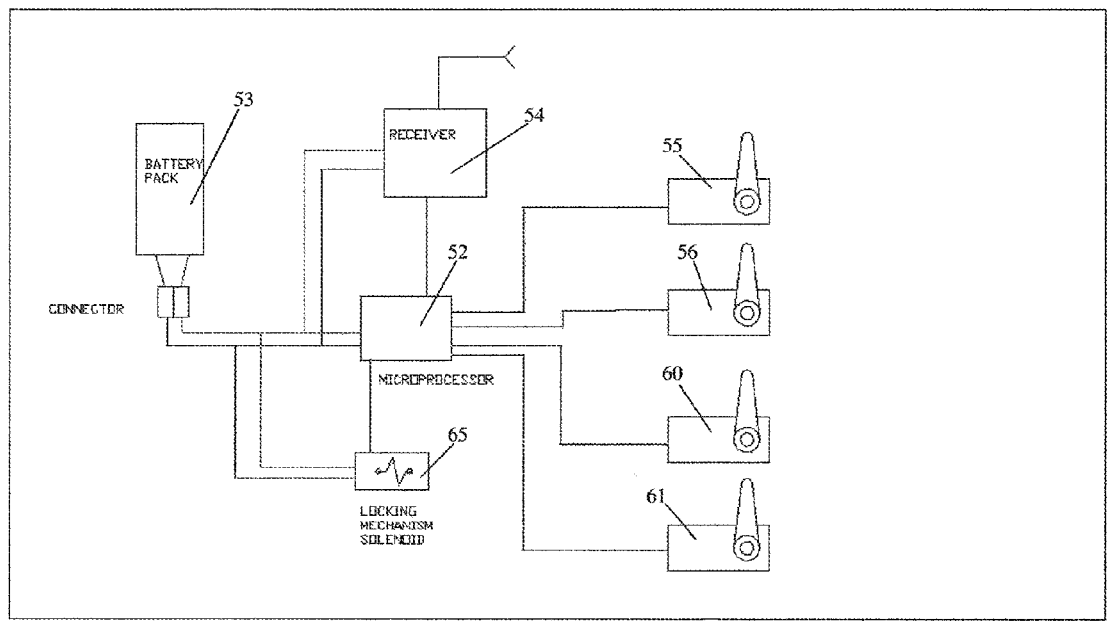
FIG. 5 is a block diagram of the on-board electronics of a growing rod device according to embodiments of the present invention.

Returning to FIG. 2, the main housing 12 of the growing rod device 10 (as well as the housing 12' of the device 10') includes an electronics housing 32. This housing contains the on-board electronics necessary to power and control the growing rod device 10/10' remotely. It is contemplated that the growing rod devices of the present invention are wholly self-contained, meaning that no physical external connections are required, such as a physical connection to an external power source or control unit. Consequently, in one embodiment, the electronics housing 32 contains on-board electronics as depicted in FIG. 5. This electronics includes a microprocessor 52 with an associated power supply 53. The power supply is capable of powering all of the on-board electronics as well as the drive motor assemblies. In one embodiment, the power supply is a battery pack of several small "watch" batteries. Alternatively, the battery pack may include one or more rechargeable batteries that can be inductively charged while remaining in situ within the patient. For instance, the power supply 53 may constitute a 7.4V Ni—Cd battery capable of holding a charge for about 30 minutes. In another embodiment the power supply is a lithium poly battery. In yet another alternative, the power supply may be an inductive power supply that is only energized when inductively (but not physically) coupled to an external device. The inductive power source may be incorporated into the patient table so that the power supply 53 is only capable of being energized or powered when the patient is resting on the table. This approach can eliminate the need for a power supply in the on-board electronics for the device 10. However, in some cases it may be desirable to maintain a small power supply or battery for the microprocessor, particularly when separate sensors are to be monitored.

The on-board electronics also includes a signal receiver 54 that is small enough to be contained within the small envelop of the electronics housing 32 but capable of receiving and transmitting a signal from within the patient. The receiver 54 may also incorporate transmitter functions to transmit information regarding the health of the growing rod device or to transmit data obtained from associated sensors. For instance, in some cases it may be desirable to include a temperature sensor within the main housing 12 to monitor the temperature of the device as it is being operated to translate the extension elements. In addition, the device may include a strain gage that monitors the strain experienced by the extension elements 16, 17 under load. The signal receiver 54 may be configured to transmit and receive RF signal. It is further contemplated that a pair of encoders may be provided that measure the amount and rate of rotation of each drive assembly 20, 21. For instance, encoders disposed within the electronics housing 32 may be arranged to respond to passage of openings 66 defined in a flange 67 of each drive rotor, such as depicted in FIG. 6.

The on-board electronics includes a microprocessor 52 that provides control signals to various motor controllers based on remotely transmitted data received by the receiver 54. The microprocessor is configured to translate the remotely transmitted movement data to command signals to a motor controller 55 coupled to the stator 22 of the drive assembly 14, and to a motor controller 56 coupled to the stator 23 of the other drive assembly 15. The motor controllers 55, 56 and associated stators may be capable of bi-directional movement, or both clockwise and counter-clockwise rotation. Alternatively, a second set of stators may be provided in each drive assembly, with one stator responsible for clockwise rotation and the other responsible for counter-clockwise movement. In this case, additional motor controllers may be provided.

Figure 11:
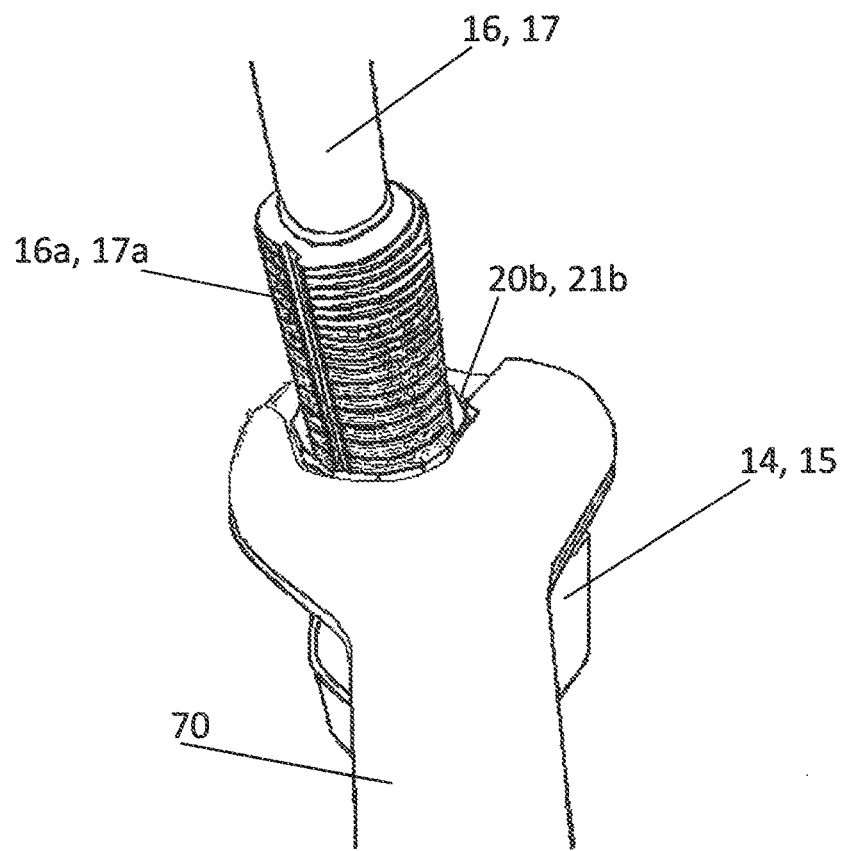
FIG. 11 is an end perspective view of a manual adjustment feature of the growing rod device shown in FIG. 2.

The drive assemblies 14, 15 may incorporate features that permit manual adjustment of the growing rod without activation of the motor controllers 55 and 56. Thus, referring to FIG. 11, the ends of the drive assemblies may be configured as a driving nut 20B, 21B (FIG. 2) that can be engaged by a tool, such as wrench 70, to manually rotate the corresponding drive assembly. Rotation of the drive assembly 14, 15 causes translation of the corresponding extension element 16, 17 as described above.

Figure 6:
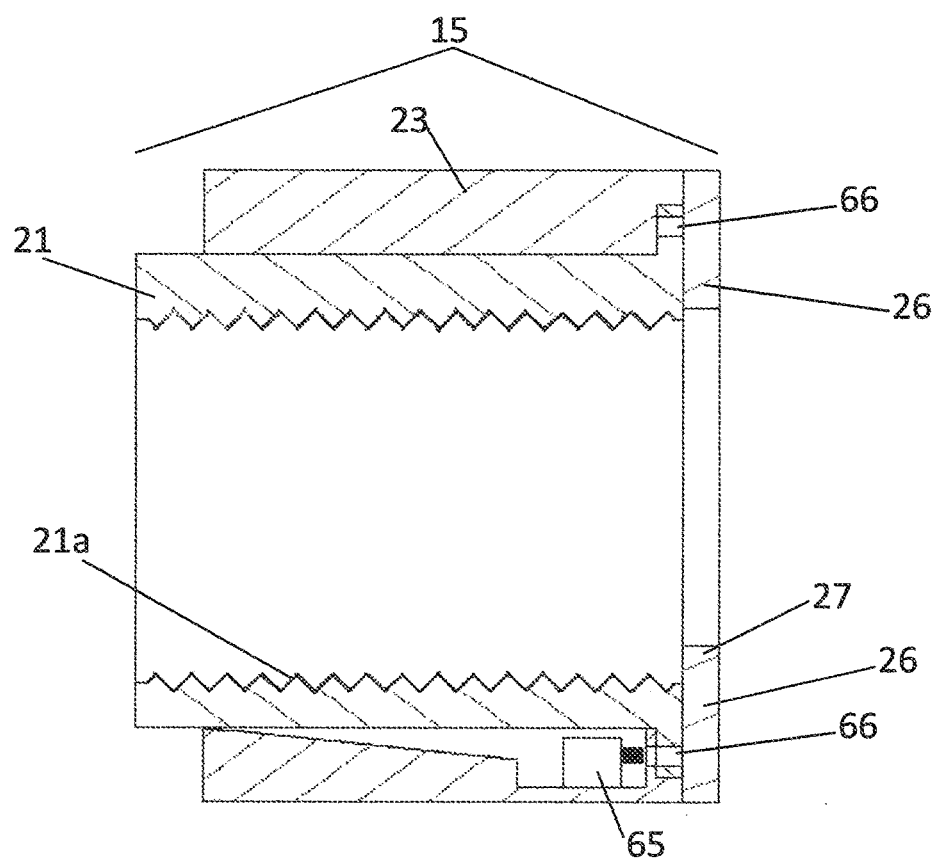
FIG. 6 is an enlarged cross-sectional view of a locking mechanism for locking the extension elements of the growing rod devices disclosed herein.

In order to ensure that the device does not collapse or extend inadvertently, the device may include a locking solenoid 65 mounted within each drive assembly, such as the drive assembly 15 shown in FIG. 6. The plunger of the solenoid is sized to be received within one of a plurality of openings 66 circumferentially spaced around a circumferential flange 67 of the drive rotor 21 (see FIG. 2). The solenoid may be configured so that the plunger is extended in the de-energized state of the solenoid. When it is desired to change the length of the device 10, the solenoid 65 is energized by the microprocessor (FIG. 5) and the plunger retracts free of the opening in the drive rotor, thereby permitting rotation of the rotor. The microprocessor may be configured to automatically extend the plunger at the end of a movement cycle and automatically retract the plunger at the beginning of the movement.

In a specific embodiment, for a growing rod device capable of spanning three or more vertebral motion segments, the main housing and drive assemblies may have a combined overall length of less than 50 mm. The extension elements may be rods each having a total length of about 60 mm. For the device 10 shown in FIG. 2, the overall retracted length of the device would be about equal to the combined length of the two extension elements, or about 120 mm. It is contemplated that each extension elements may be extended about 15 mm, leaving about 10 mm of the extension element disposed within the corresponding drive assembly, for a total extended length of about 150 mm. For the device 10' shown in FIG. 3, the extended length would be the same but the retracted length would be much less due to the telescoping or overlapping feature of this embodiment. In one specific embodiment the two extension elements 16', 17' may be configured for an overlap of about 20 mm, thereby reducing the overall retracted length of the device to about 100 mm.

The main housing and drive assemblies are formed of a medical grade material that is sufficiently strong to react the load from lengthening the extension elements. In one specific embodiment the main housing and drive assemblies are formed of a polymeric material, such as PEEK resin for the drive rotors and LP resin for the stator and main housing.

In most procedures for correction of spinal deformities, a growing rod device is implanted on either side of the spine. Thus, in the case of a scoliotic spine, a growing rod device is placed to distract the concave side of the spinal curve, or open up the concavity, while a device on the opposite convex side of the scoliotic curvature compresses the spine. The combination of the two motions ensures that the spine derotates uniformly without any lateral movement of the vertebrae. This multi-axis correction also prevents rotation of the spine about its axis. It can thus be appreciated that a typical spinal correction construct will include two growing rod devices, such as device 10 with four total extension elements 16, 17, two on each side of the spine. The task facing the caregiver/caregiver/surgeon is to provide a coordinated plan for optimum extension or retraction of the four extension elements to correct the bad curvature without introducing any other deformity conditions.

In certain embodiments it is contemplated that the multiple growing rod devices implanted within the patient are in communication, such as by a data bus coupled between the microprocessors 52 of the devices. In this instance, external communication with the devices can be limited to one primary microprocessor. The microprocessor of each device has a unique address. Software within the primary microprocessor, such as within a handheld programming unit 100 discussed below, can be configured to send control signals specific to each device and to identify transmitted data as associated with a corresponding device. This feature allows the use of multiple devices within a patient to provide multi-axis correction of the patient's spine. For instance, two devices fastened to pedicles of two vertebrae may provide correction of a scoliotic curvature in the sagittal plane, while another growing rod device fastened to a lateral surface of two vertebral bodies may provide correction of a complex curvature in the AP plane. All three growing rod devices would have a unique address. All data transmission would occur with the primary microprocessor that would then communicate with the specifically addressed growing rod device over the common data bus. As shown in FIG. 5, the microprocessor 52 may communicate with four motor controllers—the motor controllers 55, 56 discussed above associated with a growing rod device on one side of the spine, and motor controllers 60, 61 associated with a growing rod device on the opposite side of the spine. It is understood that the microprocessor 52 in FIG. 5 may represent a single microprocessor charged with controlling the four motor controllers 55, 56, 60, 61, or the microprocessor in the figure may be a representation of the separate individual microprocessors associated with each growing rod device. In the latter case, each microprocessor would be individually uniquely addressed, as described above.

Figure 7:
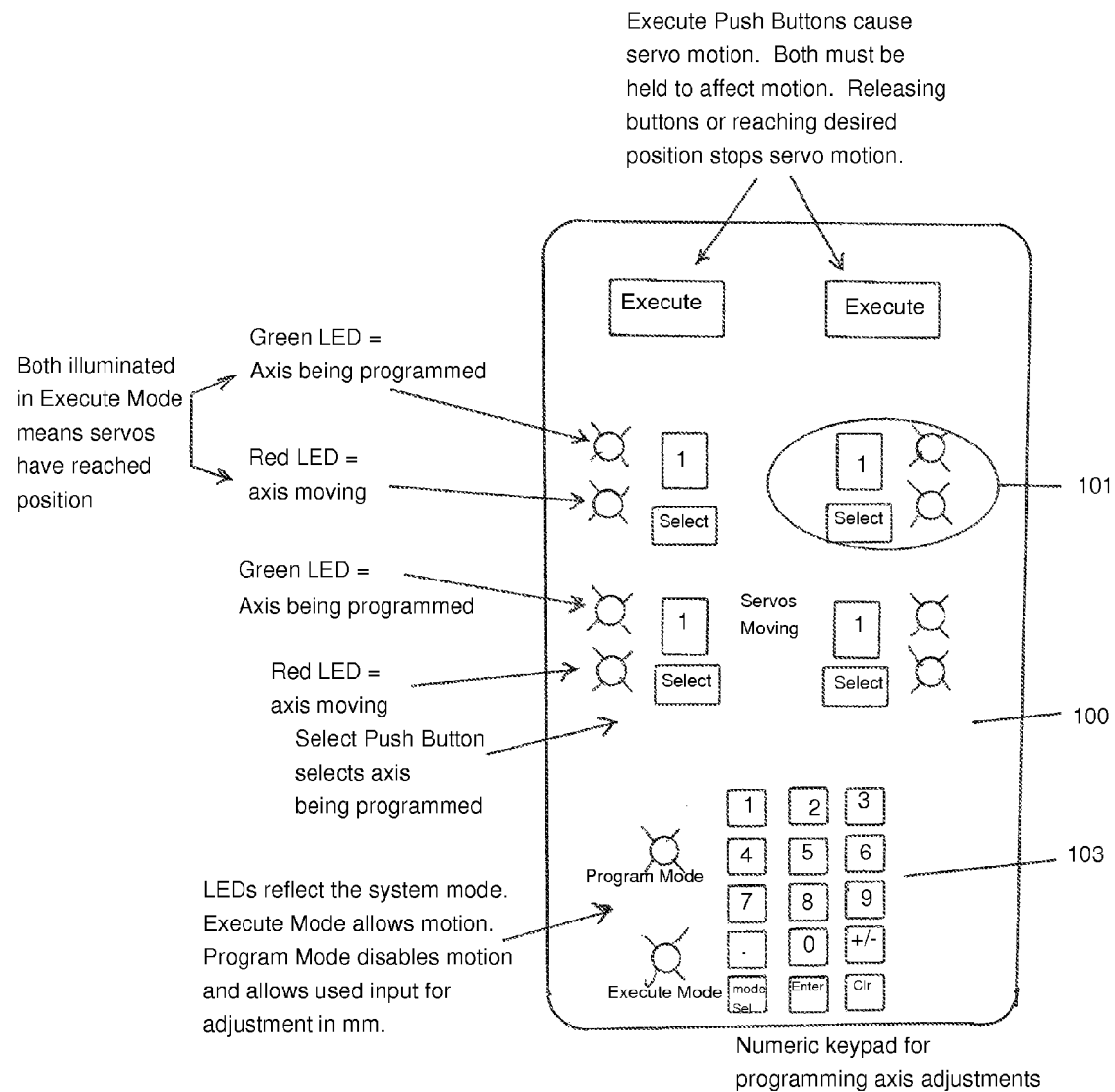
FIG. 7 is a plan view of a programming unit for use in controlling actuation of the growing rod devices in one embodiment.

The growing rod device 10 of the present invention contemplates a hand-held programming unit, 100 such as shown in FIG. 7. The programming unit includes a microprocessor and a receiver/transmitter configured for communication with the receiver/transmitter 54 of the device 10. The hand-held unit 100 may be configured to dock with a computer to up-load a distraction protocol and download data that may be obtained from the growing rod device 10. Alternatively, the unit 100 may be used to independently program each threaded rod "delta"—that is the desired extension/retraction or linear movement for each extension element. After each rod position is programmed by the physician, the pre-determined program is actuated by placing the remote programming unit in an execute mode and simultaneously pressing two "execute" buttons or keys on the programming unit coupled with the three position dead man switches. If either of the two buttons is released, the execution is halted.

In the embodiment depicted in FIG. 7, the unit 100 is configured to program and actuate four extension elements, with each element having a separate set of indicators 101. Each extension element can be successively selected by the caregiver/caregiver/surgeon to program the corresponding element. A green LED may be illuminated when a particular device is being programmed. A keypad 103 allows the caregiver/surgeon to directly input a specific delta for the given extension element. When all of the devices have been programmed the drive assembly for each extension element may be actuated by entering the "execute" mode of the programming unit 100. In order to prevent accidental activation, a pair of "execute" buttons must be depressed simultaneously and held depressed during the actuation cycle. Red LEDs and a pair of "servo moving" and "execute mode" indicators are illuminated to verify that the growing rod devices are in operation to increase or decrease their respective lengths. The activation of the devices can be terminated by releasing one or both of the "execute" buttons, or when the pre-programmed delta has been achieved for each drive assembly and extension element.

In certain embodiments the programming unit 100 is maintained by the caregiver/surgeon/physician. The unit 100 may interface with a computer system that includes software for generating an adjustment protocol for the particular patient. The software can accept data regarding the nature and extent of the spinal deformity, such as digitized data indicative of the position and orientation of vertebral landmarks. A comparison of the deformity data to an idealized spinal position for the particular patient can be used to determine the form and extent of movement of the spine necessary to approximate the ideal spinal position. This desired movement information can provide the basis for determining the incremental movements made over time, ultimately resulting in delta data for each extension element of each growing rod device. This movement protocol may thus be generated by software in the computer system, or alternatively may be determined separately by the caregiver/surgeon. This movement protocol can then be uploaded to the handheld programming unit 100.

It is further contemplated that in certain embodiments the programming unit 100 may be kept by the patient or a local care-giver. The unit 100 may be remotely programmed with movement data, such as via an Internet interface or a wireless transmission. Once the movement data is uploaded to the programming unit, the patient or local care-giver can activate the unit to effect movement of the growing rod devices implanted in the patient. In this instance, the programming unit 100 may include an inductive power source to provide power the power supply 53 of the growing rod device(s), as explained above. The patient-associated programming unit may be modified from the unit described above to eliminate the programming capabilities and to incorporate security features that disable the unit unless and until movement data has been transmitted to the unit.

Figure 8:
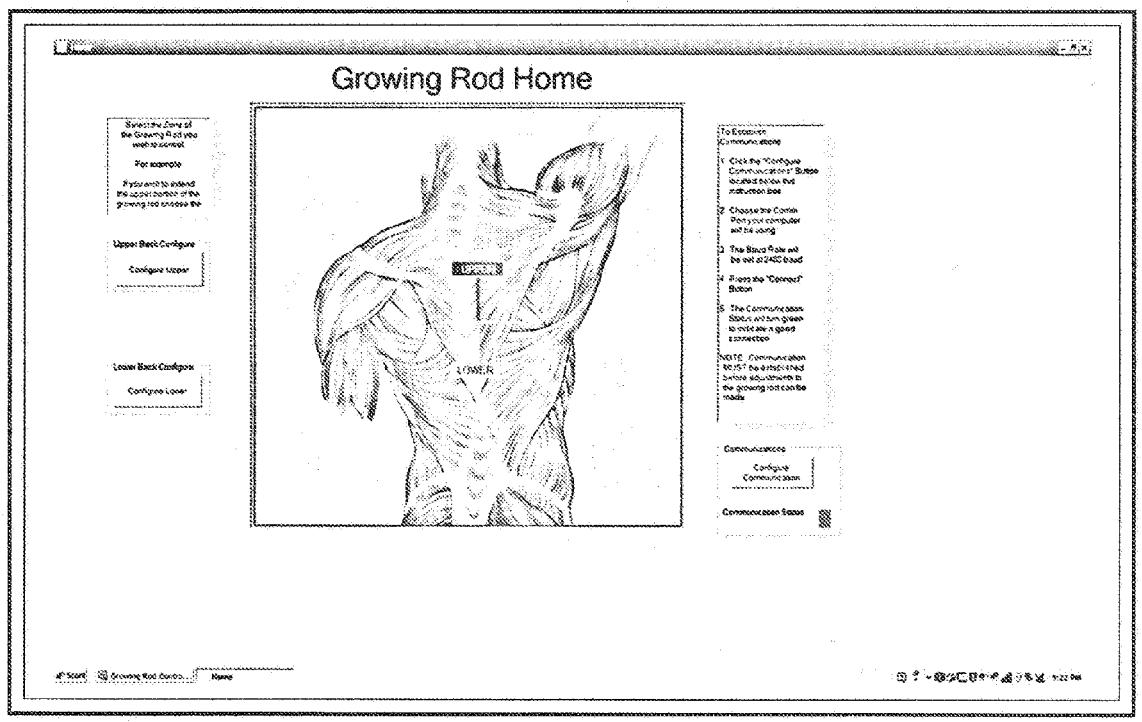
FIGS. 8-10 are screen shots of a GUI for a software program used to generate movement data or a movement protocol for growing rod device(s) implanted within a patient.
Figure 9:
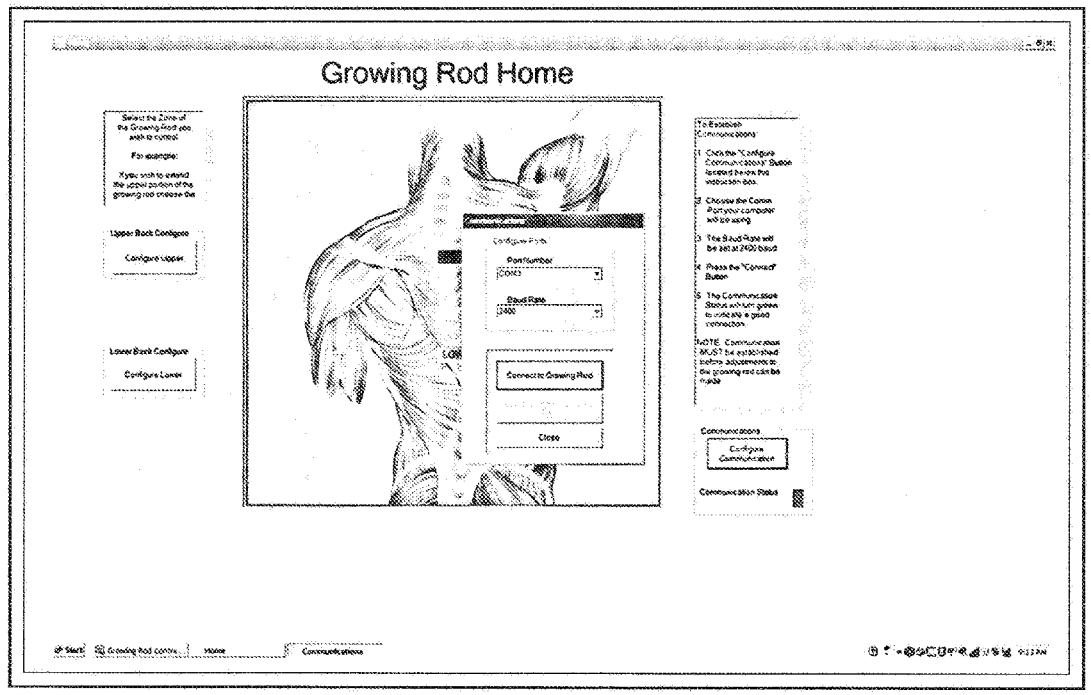
Figure 10:
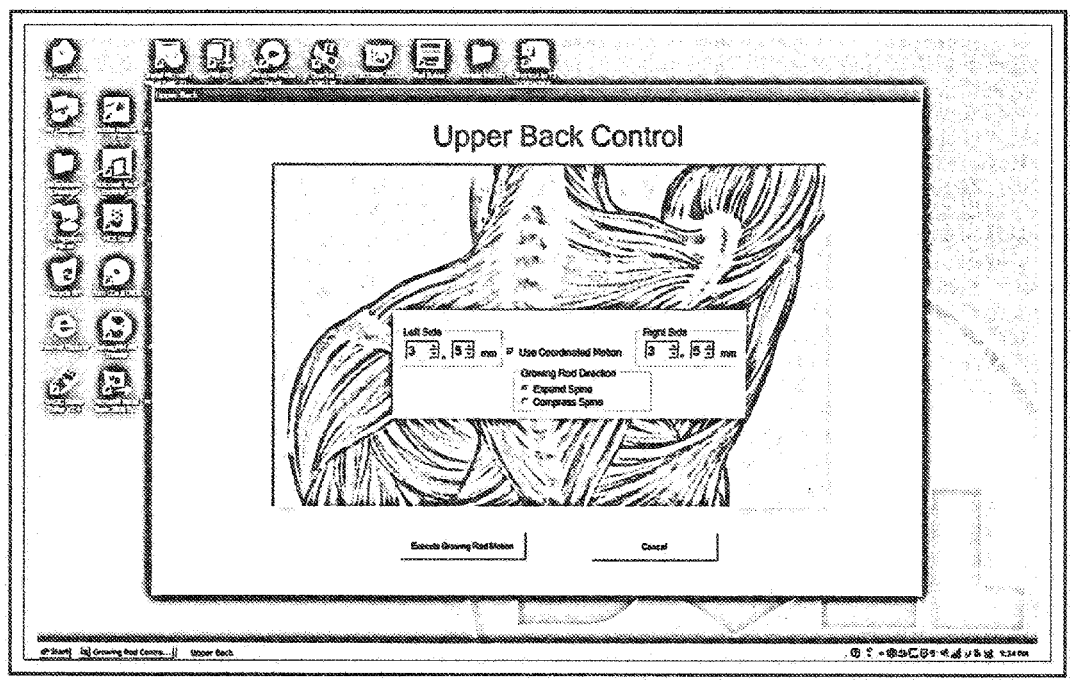

In certain embodiments, the computer program used to program the growing rod device movements may incorporate a graphical user interface that guides the caregiver/surgeon through the movement generation process. Exemplary GUI screens are shown in FIGS. 8-10. The initial screen of FIG. 8 allows the caregiver/surgeon to select the location of the growing rod devices, whether in the upper or lower back, since the movement protocols will vary depending upon whether the movement is in the lumbar or thoracic spine. The initial screen may also allow the caregiver/surgeon to establish the manner of communication of the movement protocol to the hand-held unit 100. Another GUI screen shown in FIG. 9 establishes communication with the unit 100, whether it is maintained by the caregiver/surgeon or the patient.

An exemplary GUI for programming the growing rod device movements is shown in FIG. 10. Once a particular vertebral level has been selected (in cases in which more than one pair of devices is utilized) the caregiver/surgeon can input a desired movement delta for either side of the spine. A specific entry may be made indicating whether the delta is extending or expanding the growing rod device for distraction of the spine, or compressing/retracting the device for compressing the spine. The GUI may provide means for uploading the pre-programmed movement protocol to the hand-held unit 100, or may directly interface with the growing rod devices themselves to execute the movement protocol. It is further contemplated that the software will maintain a database of the data transmitted to and from the implanted growing rod devices.

The GUI and associated software may be resident on a local computer or may be incorporated into the handheld programming device 100 with an appropriate modification to include a display screen. The software may also be implemented as an application for a more sophisticated communication device or mobile phone.

The handheld unit 100 has the capability for remote communication with the implanted growing rod device(s), including not only sending movement data but also receiving status information from the device(s). The microprocessor 52 of each growing rod device generates information as to the status of the on-board electronics as well as the drive assemblies. Fault conditions may be sensed by the microprocessor and an appropriate warning transmitted to the handheld unit 100. For instance, the on-board electronics may incorporate means for detecting the rotation of the drive rotors 20, 21 and the linear movement of the extension elements 16, 17. Real-time movement data may be transmitted to the handheld unit to provide a visual indication to the caregiver/surgeon. Lack of movement or a discrepancy between rotation of a rotor and linear movement of a corresponding extension element can generate an error signal that is transmitted to the handheld unit. As indicated above, strain gages may be associated with the extension elements to indicate loading as the device is expanded and to provide a warning if a pre-determined strain value is exceeded. Temperature sensors can transmit temperature data to the handheld unit through the on-board microprocessor.

In a further feature, the microprocessor 52 for each growing rod device 10 executes program steps for coordinated movement of the extension elements 16, 17. In a first step for using the device the surgeon or medical advisor determines the amount of lengthening or compression that should occur at the instrumented bone or spinal segment. These linear dimensions are communicated to the microprocessor for the affected growing rod device, preferably via the handheld unit 100. The microprocessor then calculates the appropriate amount of rotation of the drive motor assemblies to produce a linear displacement of the extension members to meet the requested lengthening or compression. In the illustrated embodiments, two drive assemblies 14, 15 produce the requested extension/compression which means that the two drive rotors 20, 21 are rotated. The microprocessor implements software that coordinates the movement of the two drive rotors so that the rotors are rotated at the same time. It can be appreciated that simultaneous rotation eliminates any torque concerns since an opposite torque will be applied to the two rotors by their respective drive assemblies. Moreover, it can be appreciated that the simultaneous coordinated movement of the drive rotors, and consequently the simultaneous coordinated extension/retraction of the extension members 16, 17 produces the requested movement with as little stress to the patient as possible. It is further contemplated that the microprocessor 52 is operable to move the drive rotors in opposite axial senses—i.e., one may move in compression while the other moves in distraction.

As the drive assemblies rotate the respective rotors, the amount of rotation is monitored, such as by using the encoder described above. The microprocessor 52 may evaluate the encoder signals to determine not only the amount of rotation but the rate of rotation. The microprocessor can then implement a feedback process that maintains coordinated movement of the rotors. Thus, if one rotor is rotating more quickly than the other rotor, the microprocessor can issue a control command to one drive assembly to either speed it up or slow it down, as appropriate for controlled extension/retraction. The microprocessor also evaluates the encoder signals to determine whether the movement is complete, at which time it de-energizes the drive assemblies to stop the growing rod device. At the same time the microprocessor may activate the locking solenoid 65 discussed above to lock the respective drive rotors. It is, of course, contemplated that the threads between the drive rotors and the extension elements may be configured to effectively lock the extension elements in their final position, without the need for a separate locking solenoid.

The microprocessor 52 and handheld controller 100 may include software that provides controlled coordinated movement of multiple growing rod devices. As discussed above, treatment of severe spinal deformities, such as scoliosis, often require movement of different spinal segments in different ways. In some procedures, two pairs of growing rod devices may be implanted in a patient—one pair on opposite sides of the midline at the lumbar spine and another pair on opposite sides of the midline at the thoracic spine. It can be appreciated that while the growing rod on one side of the midline must be extended to correct an improper lateral curvature of the spine, the other growing rod on the opposite side of the midline must retract or shorten. It can also be appreciated that correction of curvature in the lumbar spine will necessarily affect the thoracic spine. Consequently, coordinated simultaneous movement in both spinal levels may be desirable to provide accurate correction with as little stress to the patient and the patient's spine as possible.

As explained above, the handheld unit 100 is capable of communicating with multiple growing rod devices, each device having a unique address for wireless communication. More particularly, the microprocessor 52 associated with each growing rod device maintains the unique address so that the microprocessor only responds to signals received by the receiver 54 that carry that unique address. Thus, when the surgeon enters the adjustment data on the handheld unit the adjustment data is communicated to the associated growing rod device 10. When the surgeon activates the adjustment process (by depressing the two "execute" buttons) the handheld unit transmits an execute signal that is simultaneously received by all the growing rod devices and each such device immediately begins moving their associated extension elements 16, 17. The microprocessor of each growing rod device returns signals to the handheld unit that identifies the particular device and indicate the status of the extension element movement. If communication between the handheld unit and any one of the growing rod devices is interrupted the handheld unit transmits a stop command to each device so that further motion ceases. If any growing rod device begins to move out of sync with the other devices, the handheld unit may again issue a stop command to all devices. Alternatively, the microprocessor of the handheld unit may be programmed to issue device specific commands to adjust the extension or retraction of the particular device or devices as necessary to restore the coordinated motion among all of the growing rod devices.

The present invention further contemplates growing rod devices capable of autonomous adjustment. More specifically, the on-board microprocessor 52 for a growing rod device may execute software that follows an extension/retraction protocol that may be pre-programmed by the surgeon using the handheld unit 100. The microprocessor includes an embedded clock or timer that can be initiated when the growing rod device is initially implanted and the autonomous adjustment sequence is activated by the surgeon. The software in the on-board processor may execute software according to the flowchart shown in FIG. 12. Once the autonomous adjustment sequence is initiated the microprocessor goes into "sleep mode" where the microprocessor and device are inactive, except for various monitoring or self-monitoring functions. Examples of these monitoring functions may include the state of the on-board power supply, device temperature (which may be indicative of a physical problem with the patient), orientation of the bone segments or spine, or a change in position of the extension elements 16, 17.

Figure 12:
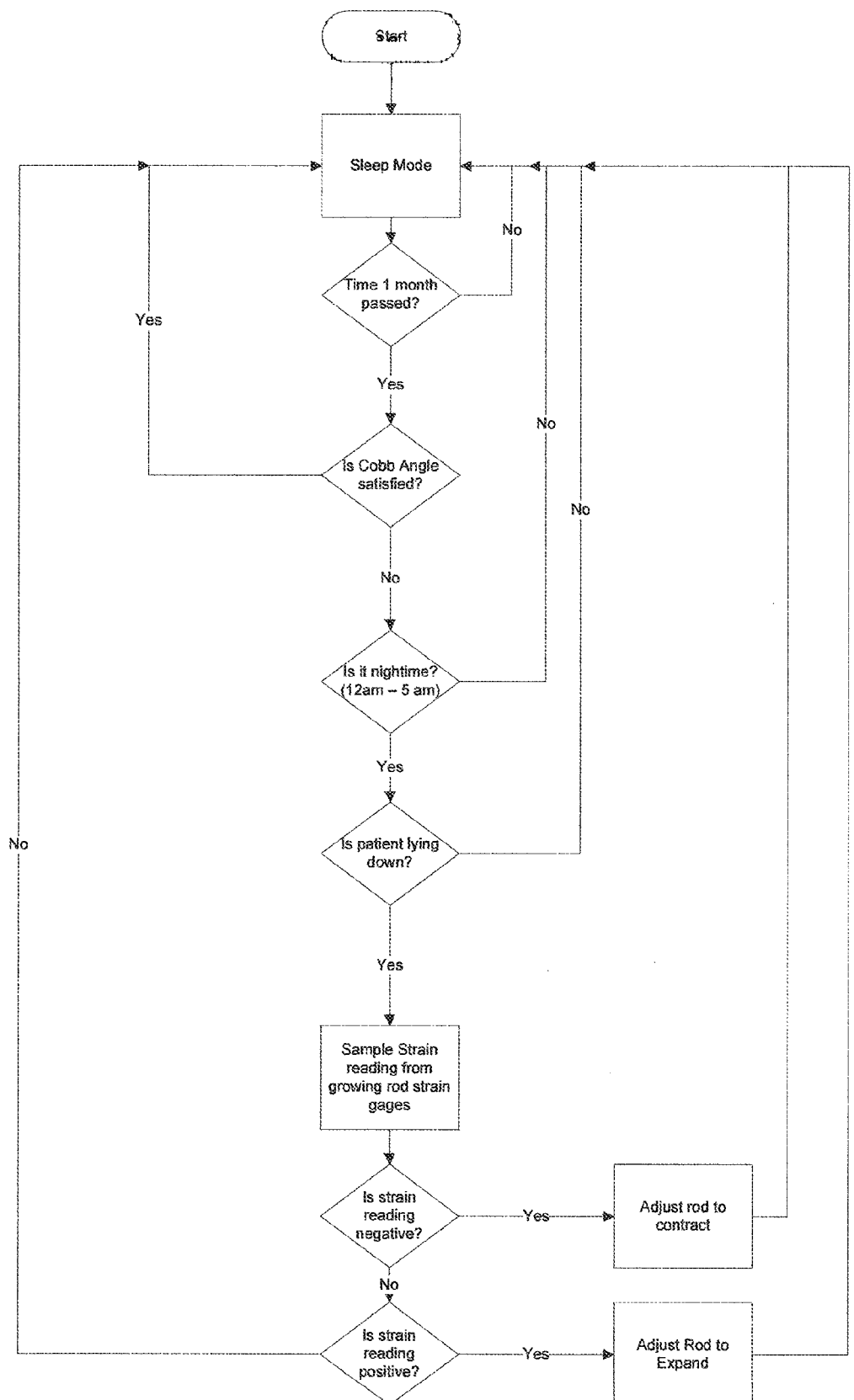
FIG. 12 is a flowchart of a software program executed by a growing rod device in an autonomous adjustment mode of operation.

During the sleep mode the microprocessor on-board clock or timer determines whether a pre-determined period has passed, such as one month in the example of FIG. 12. This time period is established by the surgeon based on the treatment protocol. For instance, in treating scoliosis the patient's spine is typically adjusted every month. This time period may be adjusted by the surgeon as appropriate for the patient and treatment protocol. In one embodiment, once the requisite time has passed, the microprocessor may determine whether the current time is at night, since it is likely that the patient is inactive and relaxed. This determination may be made by referring to an on-board real-time clock, although wireless access to a remote clock via the transmitter/receiver of the on-board electronics is contemplated. If the current time is not at night the device returns to the sleep mode until a nighttime condition is sensed. If the appropriate time is met, then the routine implement by the microprocessor 52 determines whether the patient is lying down, since the requisite length adjustments may only be made when the patient is reclined, particular for spinal adjustments. This determination may be made using body position sensors integrated into the growing rod device or carried by the patient.

Once all the pre-conditions have been met, the microprocessor may command the drive assemblies to move the extension elements 16, 17 according to the pre-programmed length adjustment protocol. In one embodiment, the movement only occurs according to the pre-programmed protocol. Alternatively, the length adjustment may be based on strain readings of the extension elements. In this embodiment, each extension element 16, 17 is outfitted with a strain gage or a series of strain gages along the length of the element. When the microprocessor determines that it is time for a length adjustment of the growing rod device, the microprocessor polls the strain gages for the extension elements. As reflected in the last steps of the flowchart in FIG. 12, the goal of monitoring the strain gage values is to produce a movement that produces an essentially zero strain state within the extension element. Thus, if the measured strain for a particular element is negative, the element is adjusted to contract, while if the measured strain is positive the extension element is extended or expanded. It is contemplated that only slight pre-determined adjustments are made and the microprocessor program loops until the accumulated adjustments have achieved the desired zero strain state. (It can be appreciated that the measured strain need not be exactly zero but may fall within a pre-determined range). Once the necessary length adjustments have been made the microprocessor returns to the sleep mode.

The software steps implemented by the microprocessor may be modified specifically for the treatment of spinal deformities, such as scoliosis. In a scoliosis condition, the patient's spine is abnormally curved in the lateral plane of the patient—i.e., from side to side. The abnormally curved portions of the spine, such as the lumbar or thoracic spine, subtend an angle known as the Cobb angle. The goal in the treatment of scoliosis is to reduce the Cobb angle to as close to zero as possible, which corresponds to a perfectly straight spine. In practice, however, it is usually not possible to achieve a zero Cobb angle, so most treatments are directed to a satisfactory ending angle, such as 7-10 degrees. In the modification reflected in the flowchart of FIG. 12, the microprocessor may determine the Cobb angle for the patient. The Cobb angle may be determined using strain gage data from the extension elements or position sensors associated with the growing rod device or the patient. For instance, fiducials may be associated with the ends of the extension elements or with particular vertebrae of the patient. The microprocessor evaluates the sensor data to calculate the Cobb angle at the particular moment in time. If the Cobb angle is within a predetermined range for the particular moment in time (i.e., is the Cobb angle satisfied) then no length adjustment is required and the device returns to the sleep mode. On the other hand, if the Cobb angle is outside the desired range, the microprocessor proceeds with the subsequent steps to adjust the growing rod length as described above.

Figure 13:
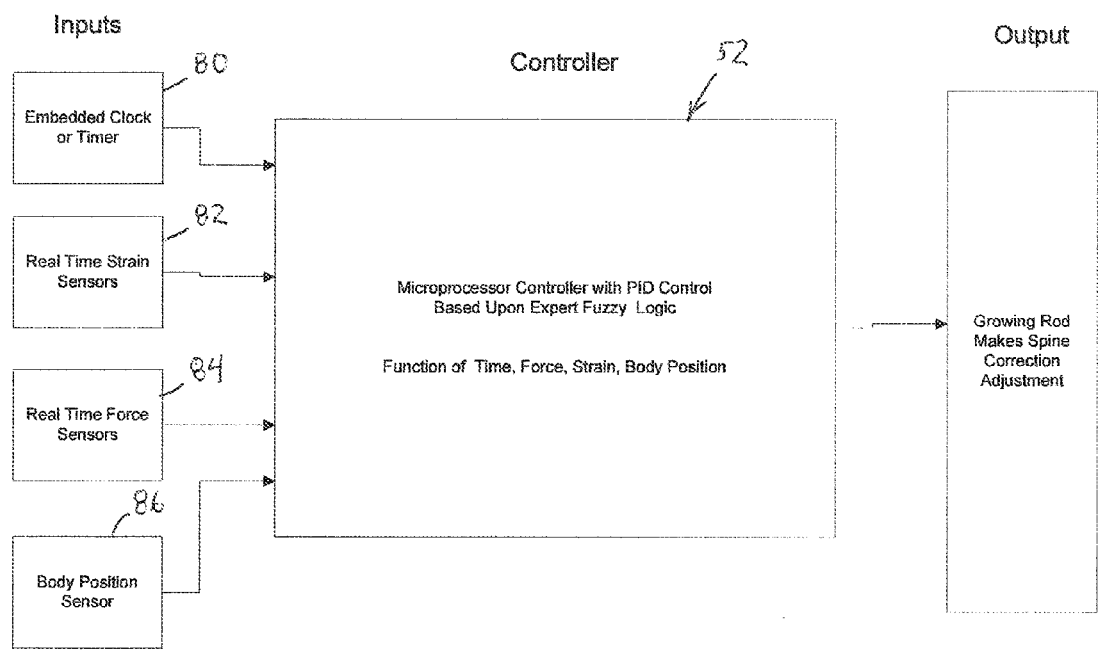
FIG. 13 is a block diagram of a controller for controlling operation of the growing rod devices disclosed herein.

In accordance with one embodiment, the microprocessor 52 for the growing rod system may follow the architecture shown in the block diagram of FIG. 13. The microprocessor may receive input signals from an embedded clock 80 and real-time strain sensors 82 as discussed above. Additional input signals may be received from real time force sensors 84 associated with the device that measure the force generated by or against the extension elements. Body position sensors 86 may also provide input signals to indicate, for instance, whether the patient is reclined. The microprocessor can incorporate a PID controller that implements expert fuzzy logic to determine the proper movement of the extension elements to achieve an ideal spine correction.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected. For instance, the present disclosure relates to the compression/distraction of the spine to correct an abnormal curvature or deformity. The automated growing rod devices disclosed herein may also be utilized to increase the length of a long bone or to assist in fracture fixation and compression.

What is claimed is:

1. A growing rod device for implantation in a patient comprising:
   a pair of elongated extension elements, each extension element including an anchor element at an anchor end thereof configured to be anchored to a portion of a patient's spinal anatomy and each including an opposite end opposite said anchor end,
   a drive assembly coupled to said opposite end of each of said extension elements, said drive assembly configured and operable to move said anchor end of said extension elements relative to each other; and
   on-board electronics associated with said drive assembly and including;
      an on-board microprocessor connected to said drive assembly and operable to activate said drive assembly to move said one or both of said extension elements;
      a power supply providing power to said on-board microprocessor and said drive assembly;
      a receiver for receiving remotely transmitted data, said receiver coupled to said on-board microprocessor to provide said data to said on-board microprocessor, said data including movement data for extending or retracting said extension element relative to said housing; and
      at least one sensor for providing data to said microprocessor indicative of the position and/or force experienced by the patient's spinal anatomy engaged to said anchor elements, said at least one sensor is configured to determine the Cobb angle of the patient's spine,
      wherein said microprocessor is configured to automatically control the amount and direction of relative movement of said extension elements as a function of the sensor data to achieve a predetermined Cobb angle.

2. The growing rod device of claim 1, wherein said at least one sensor includes at least one strain gage associated with at least one of said extension elements.

3. The growing rod device of claim 1, further comprising a housing containing said drive assembly and said microprocessor.

4. The growing rod device of claim 1, further comprising a locking device operable to prevent relative movement of said extension elements.

5. The growing rod device of claim 1, wherein said power supply is an inductive power supply configured to inductively receive energy from an external power source.

6. The growing rod device of claim 5, wherein said external power source is incorporated into a handheld unit.

7. The growing rod device of claim 1, wherein said anchor element includes a slotted plate configured for engagement to the patient's anatomy with a bolt or screw.

8. The growing rod device of claim 1, wherein said microprocessor is configured to execute software operable to produce controlled relative movement of said two extension elements to minimize the strain measured by said at least one sensor.

9. The growing rod device of claim 1, wherein said on-board microprocessor is configured to execute software adapted to automatically activate said drive assembly at a predetermined time.

10. The growing rod device of claim 1, wherein:
said at least one sensor includes a sensor to adapted to evaluate the physical position of the patient; and
said on-board microprocessor is configured to only activate said drive assembly only when the patient is in a predetermined position.

11. A growing rod device for implantation in a patient comprising:
a pair of elongated extension elements, each extension element including an anchor element at an anchor end thereof configured to be anchored to a portion of a patient's spinal anatomy and each including an opposite end opposite said anchor end;
a drive assembly coupled to said opposite end of each of said extension elements, said drive assembly configured and operable to move said anchor end of said extension elements relative to each other;
on-board electronics associated with said drive assembly and including;
an on-board microprocessor connected to said drive assembly and operable to activate said drive assembly to move said one or both of said extension elements;
a power supply providing power to said on-board microprocessor and said drive assembly;
a receiver for receiving remotely transmitted data, said receiver coupled to said on-board microprocessor to provide said data to said on-board microprocessor, said data including movement data for extending or retracting said extension element relative to said housing; and
at least one sensor for providing data to said microprocessor indicative of the position and/or force experienced by the patient's spinal anatomy engaged to said anchor elements; and
a handheld unit providing an interface between said on-board microprocessor and a caregiver, said handheld unit including means for communicating data to said on-board microprocessor indicative of a desired relative movement of said extension elements,
wherein said microprocessor is configured to automatically control the amount and direction of relative movement of said extension elements as a function of the sensor data.

12. The growing rod device of claim 11, wherein:
said at least one sensor is configured to determine the Cobb angle of the patient's spine; and
said microprocessor is configured to control the relative movement of said extension elements to achieve a predetermined Cobb angle.

13. The growing rod device of claim 11, wherein:
said handheld unit includes;
a numeric keypad for caregiver entry of a desired movement data; and
a transmitter for transmitting said data to said receiver; and
software resident within said handheld unit and/or said on-board microprocessor for translating said movement data into movement commands for controlling said drive assembly.

* * * * *